(12) United States Patent
Chen et al.

(10) Patent No.: US 10,351,857 B2
(45) Date of Patent: Jul. 16, 2019

(54) **MARINE BACTERIAL GENE *LFLIZ* AND USE**

(71) Applicant: SHANDONG UNIVERSITY, Jinan (CN)

(72) Inventors: Xiulan Chen, Jinan (CN); Yuzhong Zhang, Jinan (CN); Ang Liu, Jinan (CN); Xiaoyan Song, Jinan (CN); Yang Yu, Jinan (CN); Pingyi Li, Jinan (CN); Xiying Zhang, Jinan (CN); Mei Shi, Jinan (CN); Binbin Xie, Jinan (CN); Hainan Su, Jinan (CN); Qilong Qin, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 15/765,024

(22) PCT Filed: Oct. 24, 2016

(86) PCT No.: PCT/CN2016/103059
§ 371 (c)(1),
(2) Date: Mar. 30, 2018

(87) PCT Pub. No.: WO2017/215174
PCT Pub. Date: Dec. 21, 2017

(65) Prior Publication Data
US 2019/0048353 A1    Feb. 14, 2019

(30) Foreign Application Priority Data

Jun. 15, 2016  (CN) .......................... 2016 1 0430027

(51) Int. Cl.
| | | |
|---|---|---|
| *C12P 21/04* | (2006.01) | |
| *C12N 15/70* | (2006.01) | |
| *C07K 14/195* | (2006.01) | |
| *C12P 19/30* | (2006.01) | |
| *C12P 19/32* | (2006.01) | |
| *C07K 1/16* | (2006.01) | |
| *C07K 1/34* | (2006.01) | |

(52) U.S. Cl.
CPC ................ *C12N 15/70* (2013.01); *C07K 1/16* (2013.01); *C07K 1/34* (2013.01); *C07K 14/195* (2013.01); *C12P 19/30* (2013.01); *C12P 19/32* (2013.01)

(58) Field of Classification Search
CPC .............................. C07K 14/195; C12N 15/70
See application file for complete search history.

(56) References Cited

PUBLICATIONS

Liu et al., ACS Chem. Biol. (2016) vol. 11, pp. 2414-2419.*
Accession No. WP_013464393, May 14, 2017.*
PCT/CN2016/103059, Written opinion—English Translation, (2016).*

* cited by examiner

*Primary Examiner* — Tekchand Saidha
(74) *Attorney, Agent, or Firm* — CBM Patent Consulting, LLC

(57) ABSTRACT

It relates to a L*fli*Z gene and its application. The sequence of gene L*fli*Z is shown in SEQ ID NO.1. This invention also relates to the recombinant protein L*fli*Z encoded by L*fli*Z gene and its application in preparation of 2', 3'-cNMPs. The recombinant L*fli*Z protein encoded by gene L*fli*Z can bind four kinds of 2', 3'-cNMPs during its expression in *Escherichia coli*. Four kinds of 2', 3'-cNMPs can be prepared simultaneously from the recombinant *E. coli* by extracting the recombinant protein L*fli*Z. The yield of 2', 3'-cNMPs reaches 2.5 mg/L fermentation broth by the method in the present invention, indicating that this method has a good application potential.

Figure 1:
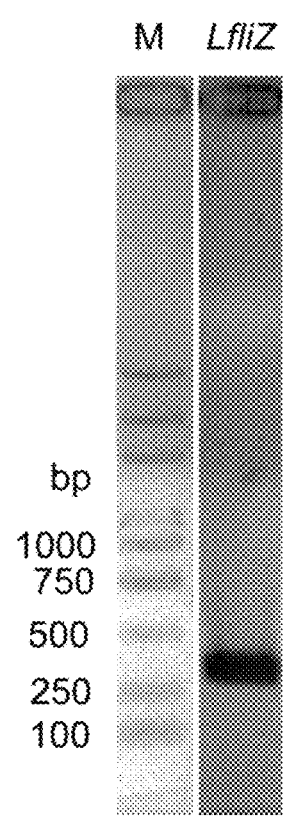

12 Claims, 6 Drawing Sheets
Specification includes a Sequence Listing.

MARINE BACTERIAL GENE *LFLIZ* AND USE

TECHNICAL FIELD

The present invention relates to gene L*fliZ* from a marine bacterium and its application, which belongs to biotechnological field.

BACKGROUND

There are a huge number of microorganisms in the sea, including a plenty of unexploited new species and new gene resources. With the development of technology, exploitation of marine microbial resources has become a research hotspot all over the world. However, owing to the difficulties in sampling and cultivating, the exploitation and utilization of marine microbial and their genetic resources is still limited. Mining new genes and studying their functions is of great significance for the exploitation and utilization of marine microbial resources.

Cyclic nucleotides are important second messengers in living cells, involving in a range of intracellular physiological pathways. It was found that 3',5'-cAMP, 3',5'-cGMP, 3',5'-cCMP, 3',5'-cUMP, c-di-GMP, c-di-AMP and cGAMP are all second messengers to regulate intracellular signaling pathways. In addition, 2',3'-cAMP are found in human kidney cells and mammal brain cells, 2', 3'-cAMP and 2', 3'-cGMP in plant cells, and 2', 3'-cCMP and 2', 3'-cUMP in *Pseudomonas fluorescens*. Recent studies showed that these four kinds of 2', 3'-cNMPs are likely a new type of second messengers. Due to the important physiological roles they may play, 2', 3'-cNMPs have attracted more and more attention, and therefore, there will be an increasing demand of 2', 3'-cNMPs in scientific research and pharmaceutical application. So far, all available 2', 3'-cNMPs are chemically synthesized. However, chemical synthesis have disadvantages such as low yield and high price, which limit the application of 2',3'-cNMPs to some extent.

SUMMARY OF THE INVENTION

To overcome the limitation of current technology, a method is provided in this invention to prepare four kinds of 2',3'-cNMPs (2',3'-cAMP, 2',3'-cGMP, 2',3'-cCMP and 2',3'-cUMP) rapidly by using a marine bacterial gene L*fliZ*.

DETAILED DESCRIPTION

Marine bacterial gene L*fliZ*, its nucleotide sequence is shown as SEQ ID NO.1.

The recombinant protein L*fliZ* expressed by gene L*fliZ*, its amino acid sequence is shown as SEQ ID No.2.

A recombinant vector, containing the above marine bacterial gene L*fliZ*. The preferred plasmid in the present invention is pET-22b (+).

A recombinant cell, obtained by transferring the above recombinant vector into a host cell. The preferred host cell in the present invention is *Escherichia coli*, further preferably, it is *Escherichia coli* BL21 (DE3).

The application of the above marine bacterial gene L*fliZ* in preparation of 2', 3'-cNMPs comprises steps of: (1) amplify the nucleotide sequence of marine bacterial gene L*fliZ* as shown in SEQ ID NO.1; (2) construct a recombinant vector containing the nucleotide sequence shown in SEQ ID NO.1; (3) construct a recombinant strain containing the recombination vector from step 2; (4) cultivate the recombinant strain, purify the recombinant protein L*fliZ* and prepare 2', 3'-cNMPs from recombinant protein L*fliZ*.

The preferred procedure of the present invention for strain cultivation in step (4) is as follows: cultivate the recombinant strain at 150-200 rpm and 35-38° C. until the $OD_{600}$ of the culture reaches 0.8; then incubate the culture at 100-140 rpm and 18-22° C. for 25~30 min; add 0.1 mM isopropyl-β-D-thiogalactopyranoside (IPTG) to the culture as an inducer and further cultivate the strain at 100-140 rpm and 18-22° C. for 22-25 hours.

The preferred culture medium of the present invention in step (4) is Luria-Bertani (LB) medium (one liter medium contains 10 g NaCl, 10 g peptone and 5 g yeast extract dissolved in distilled water, pH 8.0).

The preferred procedure for preparation of 2', 3'-cNMPs in step 4 is: (i) break the cells collected from the strain culture, centrifuge the cell extract, collect the supernatant, and purify recombinant protein L*fliZ* from the supernatant by $Ni^{2+}$-nitrilotriacetic acid resin; (ii) incubate the L*fliZ* protein solution from (i) for 2.5-3.5 days at −1-2° C., centrifuge the solution, collect the supernatant, and ultrafiltrate the supernatant to obtain the 2', 3'-cNMP crude extract; (iii) prepare four kinds of 2', 3'-cNMPs from the crude extract by high-performance liquid chromatographic (HPLC) with a $C_{18}$ reversed-phase column.

The preferred purification procedure of the present invention by $Ni^{2+}$-nitrilotriacetic acid resin in step (i) is as follows:

Load the supernatant on a nickel column containing 2 ml nickel gel; equilibrate the column with 20 ml lysis buffer (50 mM Tris-HCl, 150 mM NaCl, pH 8.0) after the supernatant flows through the nickel column; wash the column with 20 ml washing buffer (50 mM Tris-HCl, 150 mM NaCl, 20 mM imidazole, pH 8.0); elute the column with 10 ml elution buffer (50 mM Tris-HCl, 150 mM NaCl, 250 mM imidazole, pH 8.0), and collect the eluent that contains recombinant protein L*fliZ*.

The preferred molecular weight cutoff of the present invention for ultrafiltration in step (ii) is 3000 Da.

The preferred protocol of the present invention in step (iii) is as follows (the values are times in minutes and percentage of buffer B used): 0.0, 0; 2.5, 0; 5.0, 30; 10.0, 60; 14.0, 100; 21.0, 100; 22.0, 50 and 23.0, 0 at a flow rate of 10 ml/min. The detection wavelength is 254 nm.

The preferred mobile phases of the present invention in step (iii) used in the gradient program are as follows: buffer A (10 mM ammonium acetate, pH 5.0) and buffer B (75% (v/v) buffer A, 25% (v/v) methanol).

Beneficial Effects

In the present invention, protein L*fliZ* encoded by gene L*fliZ* is capable of binding four kinds of 2', 3'-cNMPs (2', 3'-cAMP, 2', 3'-cGMP, 2', 3'-cCMP and 2', 3'-cUMP) when expressed in *E. coli*. This invention offers a method for preparation four kinds of 2', 3'-cNMPs simultaneously from recombinant *E. coli* by purifying the recombinant protein L*fliZ*, with a high production of 2.5 mg 2', 3'-cNMPs/L fermentation broth, indicating that it has a good application potential.

FIGURE LEGENDS

FIG. 1. Agarose gel electrophoretic analysis for gene L*fliZ* amplified by PCR. M: DNA marker; L*fliZ*: gene L*fliZ*.

Figure 2:
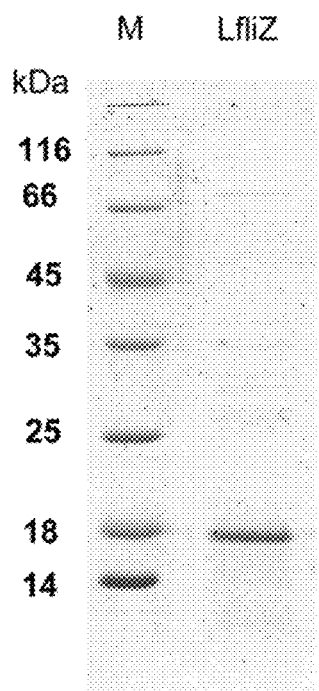

FIG. 2. SDS-PAGE analysis of recombinant protein LfliZ purified by Ni$^{2+}$-nitrilotriacetic acid resin. M: protein marker; LfliZ: recombinant protein LfliZ.

Figure 3:
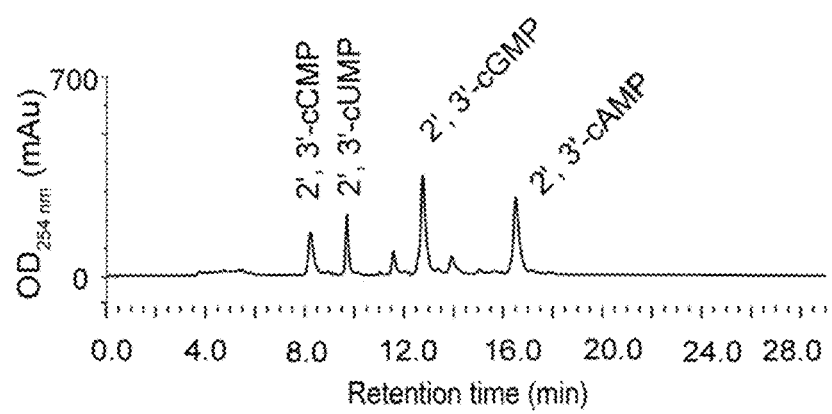

FIG. 3. HPLC separation of four kinds of 2', 3'-cNMPs in the filtrate.

Figure 4:
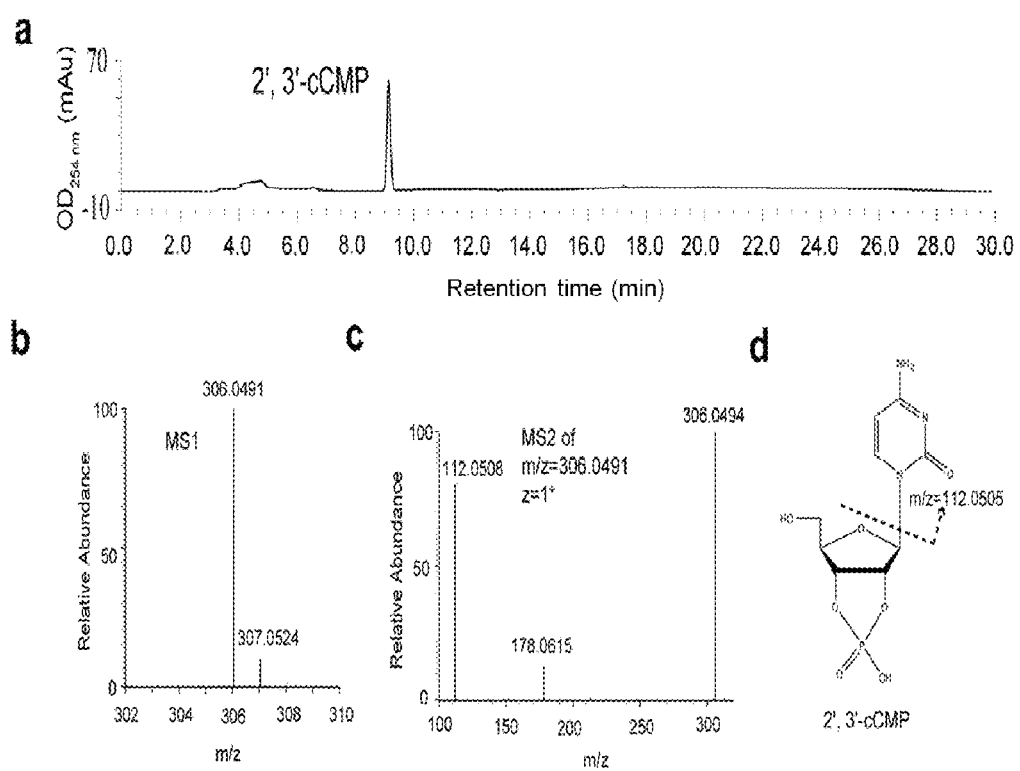

FIG. 4. HPLC and LC-MS analyses of purified 2', 3'-cCMP includes: HPLC analysis of purified 2', 3'-cCMP (a); LC-MS analysis of purified 2', 3'-cCMP, the m/z ratio of purified 2', 3'-cCMP is 306.0491 (z=1), corresponding with the theoretical value 306.0486 (b); the structure of 2', 3'-cCMP (c).

Figure 5:
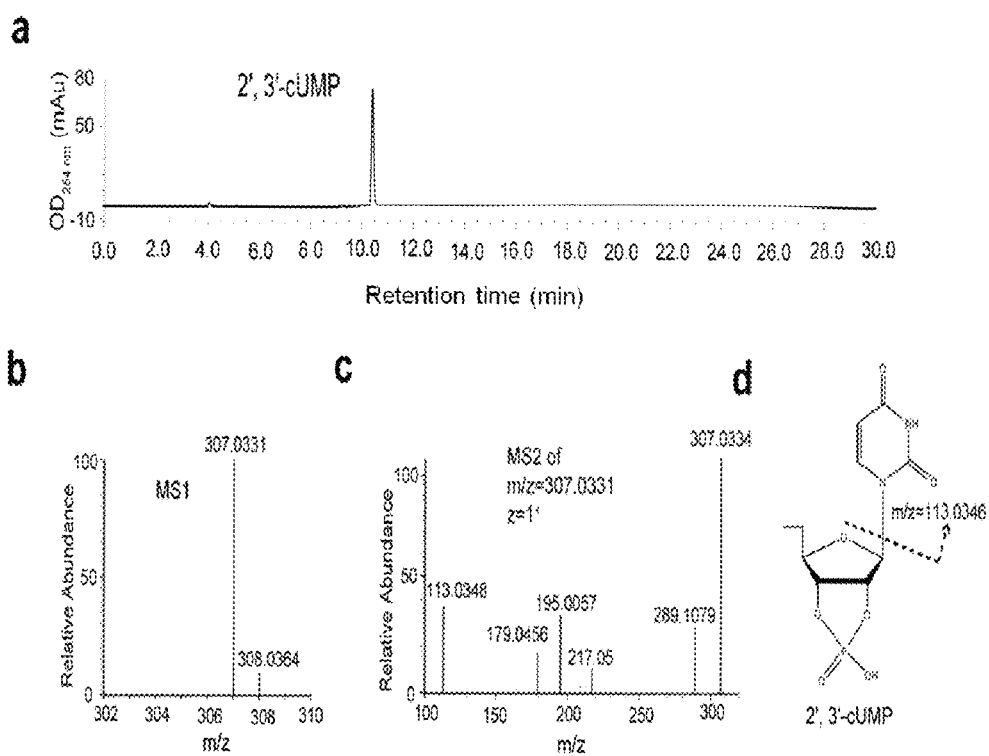

FIG. 5 HPLC and LC-MS analyses of purified 2', 3'-cUMP includes: HPLC analysis of purified 2', 3'-cUMP (a); LC-MS analysis of purified 2', 3'-cUMP, the m/z ratio of purified 2', 3'-cUMP is 307.0331 (z=1), corresponding with the theoretical value 307.0326 (b); the structure of 2', 3'-cUMP (c).

Figure 6:
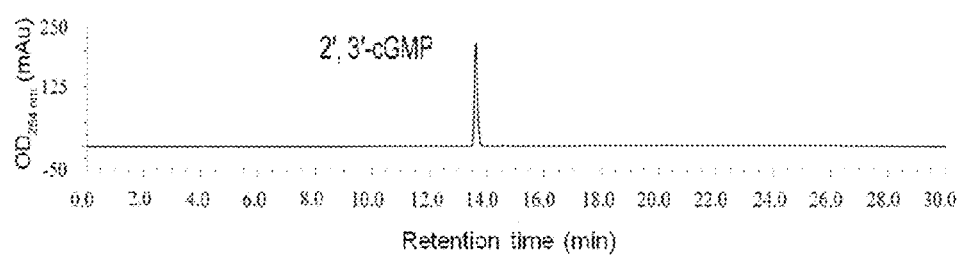
Figure 6:
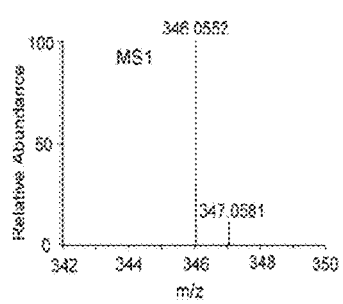
Figure 6:
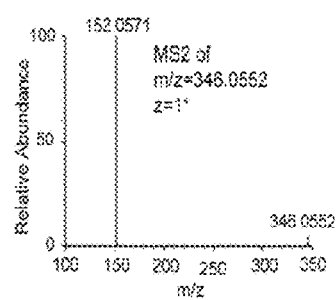
Figure 6:
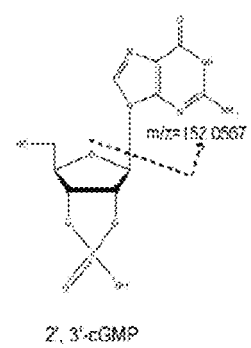

FIG. 6 HPLC and LC-MS analyses of purified 2', 3'-cGMP includes: HPLC analysis of purified 2', 3'-cGMP (a); LC-MS analysis of purified 2', 3'-cGMP, the m/z ratio of purified 2', 3'-cGMP is 346.0552 (z=1), corresponding with the theoretical value 346.0547 (b); the structure of 2', 3'-cGMP (c).

Figure 7:
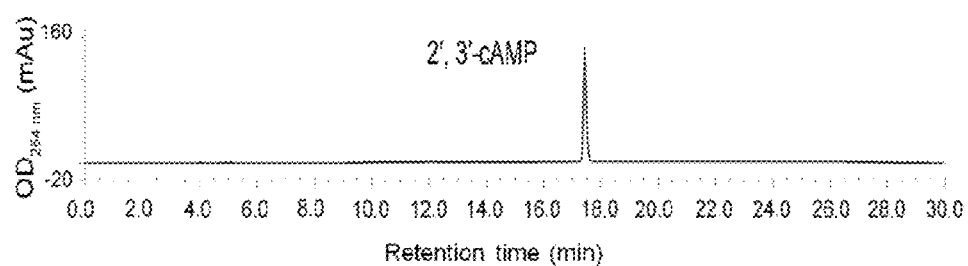
Figure 7:
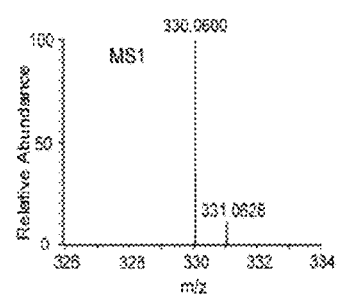
Figure 7:
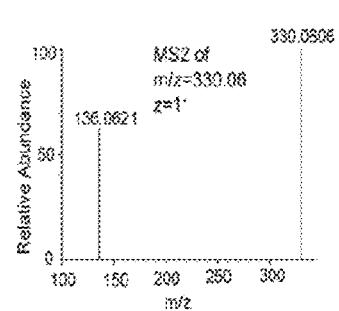
Figure 7:
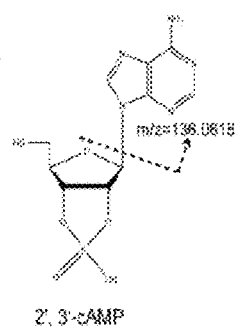

FIG. 7 HPLC and LC-MS analyses of purified 2', 3'-cAMP includes: HPLC analysis of purified 2', 3'-cAMP (a); LC-MS analysis of purified 2', 3'-cAM, the m/z ratio of purified 2', 3'-cAMP is 330.06 (z=1), corresponding with the theoretical value 330.0598 (b); the structure of 2', 3'-cAMP (c).

ILLUSTRATIVE EMBODIMENTS

The following examples are offered to illustrate, but not to limit the present invention.

Sample Source

E. coli DH5α and E. coli BL21 (DE3), TransGen Biotech Company, China;

pET-22b (+) expression plasmid, Novagen Company, America;

PCR amplification kit, TransGen Biotech Company, China;

Restriction enzymes and ligase Solution I, Takara Biomedical Technology (Beijing) Co., China;

Bacterial genome extraction kit and plasmid miniprep purification kit, Beijing Biotech Corporation, China;

Gel extraction kit, Omega bio-tek Company, America;

2', 3'-cCMP and 2', 3'-cAMP, Sigma-Aldrich Corporation, America;

2', 3'-cUMP, 2', 3'-cGMP, 3',5'-cCMP, 3',5'-cUMP, 3',5'-cGMP and 3',5'-cAMP, Biolog Company, America;

Ampicillinum and IPTG, Merck Company, America;

Methanol, Kemiou chemical reagent Company, China;

Peptone and yeast extract, Oxoid Ltd, England;

DNA sequencing, performed by Beijing Biosune Biotechnology Corporation, China;

Primer synthesis, performed by BGI Company, China;

*Pseudoalteromonas* sp. SM9913 (hereafter *Ps*. sp. SM9913), purchased from China Center for Type Culture Collection (CCTCC), and the deposited number is CCTCC NO. M2010223.

Example 1

Method for gene LfliZ cloning and expression vector construction comprises steps of:

1. Cloning of Gene LfliZ 1.1. Extraction of Genomic DNA from *Ps*. Sp. SM9913

The genomic DNA of *Ps*. sp. SM9913 was extracted according to the instructions of genome extraction kit from Biotech Corporation.

1.2. Design and Synthesis of the Primers

Primers were designed according to the LfliZ gene sequence. The primer sequences were as follows:

```
F:
                                    (SEQ ID NO: 3)
GGAATTCCATATGAGTAACCAATCAG;

R:
                                    (SEQ ID NO: 4)
CCGCTCGAGTGCATTGGTTTTTTTGC.
```

Primers were synthesized by Sangon Biotech (Shanghai) Co., Ltd, China.

1.3 Amplification of Gene LfliZ by PCR and its Recovery (1) The LfliZ gene sequence was amplified with primers F and R, using the genomic DNA of *Ps*. sp. SM9913 as template. PCR reaction conditions was as follows: pre-denaturing at 95° C. for 5 min; denaturing at 95° C. for 30 sec; annealing at 55° C. for 30 sec; extending at 72° C. for 30 sec; 30 cycles; extending ultimately at 72° C. for 5 min.

The PCR amplification system (50 μl) was as follows:

| | |
|---|---|
| Sterilized distilled water | 32.2 μl |
| 5× TransStart FastPfu buffer | 10 μl |
| dNTP mix | 5 μl |
| Primer F (50 μM) | 0.4 μl |
| Primer R (50 μM) | 0.4 μl |
| Genomic DNA | 1 μl |
| TransStart FastPfu DNA polymerase | 1 μl |

(2) The PCR products were subjected to 1% agarose gel electrophoresis. The DNA fragment of gene LfliZ was recovered with DNA purification kit from Omega.

2. Construction of the Recombinant Expression Vector and Strain.

(1) Digestion of gene and the expression vector

The LfliZ gene and vector pET-22b were digested with restriction enzymes Nde I and Xho I. The digestion reaction system was as follows:

| | |
|---|---|
| Buffer | 2 μl |
| Expression plasmid pET-22b/gene LfliZ | 8 μl |
| Restriction enzyme Nde I | 1 μl |
| Restriction enzyme Xho I | 1 μl |
| Sterilized distilled water | 8 μl |

The samples were mixed smoothly and centrifuged for 2 sec and then incubated at 37° C. for 30 min.

(2) The digested products were subjected to 1% agarose gel electrophoresis, and then the objective DNA fragments were recovered with DNA purification kit from Omega.

(3) The digested gene LfliZ and vector pET-22b from step (2) were ligated

The reaction system was as follows:

| | |
|---|---|
| Digested vector pET-22b | 1 μl |
| Digested gene LfliZ | 4 μl |
| Solution I | 5 μl |

The sample was mixed smoothly and centrifuged for 2 sec and then incubated at 16° C. overnight.

(4) The recombinant expression vector pET-22b-L*fliZ* obtained from step (3) was transformed into *E. coli* BL21 (DE3) according to the method described in Molecular Cloning Manual. The procedure comprises steps of: mix the ligation solution with *E. coli* BL21 (DE3) competent cells, and ice bath the mixture for 30 min; water bath the mixture at 42° C. for 90 s; immediately transfer into ice bath to cool down the mixture for 1-2 min; add 500 μl liquid LB medium, and incubate the mixture at 37° C. for 1 h; centrifuge the mixture, discard the supernatant and resuspended the bacterial cells with 100 μl LB liquid medium, then spread the cells on a Maconey agar plate containing 100 μg/ml ampicillin and incubate the plate at 37° C. overnight to form colonies of the recombinant strain.

The recombinant strain was verified by plasmid sequencing in Sangon Biotech (Shanghai) Co., Ltd.

The DNA sequence of gene L*fliZ* was showed in SEQ ID NO. 1.

Example 2

1. Fermentative Cultivation of the Recombination Strain (1) Inoculum preparation: the recombinant strain obtained in example 1 was inoculated into liquid LB medium containing 100 μg/ml ampicillin, which was then cultivated at 180 rpm and 37° C. overnight to prepare the inoculum.

(2) The inoculum from step (1) was inoculated in 1 L fermentation medium with 1% inoculum size and cultivated at 37° C., 180 rpm until the $OD_{600}$ of the culture reached 0.8, and then the culture was incubated at 20° C., 120 rpm for 30 min. After that, 0.1 mM IPTG was added in the culture which was then further cultivated at 20° C., 120 rpm for 24 hours.

The ingredients of 1 liter LB liquid medium (pH 8.0) were as follows: 10 g NaCl, 10 g peptone, and 5 g yeast extract, dissolved in distilled water.

2. Purification of Protein L*fliZ* (1) Buffers used for purification

Lysis buffer: 50 mM Tris-HCl, 150 mM NaCl, pH 8.0

Washing buffer: 50 mM Tris-HCl, 150 mM NaCl, 20 mM imidazole, pH 8.0

Elution buffer: 50 mM Tris-HCl, 150 mM NaCl, 250 mM imidazole, pH 8.0 (2) The cells in the fermentative culture from step 1 were collected and resuspended with 50 ml lysis buffer (for 1 liter medium), and then were broken at the pressure of 1000 bar.

(3) The solution from step (2) was centrifuged at 4° C., 12,000 rpm for 50 min.

(4) The supernatant from step (3) was loaded on a nickel column filled with 2 ml nickel gel. After the supernatant flowed through the nickel column, the column was equilibrated with 20 ml lysis buffer, and then washed with 20 ml washing buffer (50 mM Tris-HCl, 150 mM NaCl, 20 mM imidazole, pH 8.0). After that, the recombinant protein L*fliZ* was eluted with 10 ml elution buffer (50 mM Tris-HCl, 150 mM NaCl, 250 mM imidazole, pH 8.0). The eluent containing protein L*fliZ* was collected. SDS-PAGE analysis of the purified protein L*fliZ* was shown in FIG. 2.

The protein sequence of L*fliZ* was shown in SEQ ID NO. 2.

Example 3

1. Preparation of the Solution Containing 2', 3'-cNMPs.

(1) The solution of protein L*fliZ* obtained from example 2 was incubated at 0° C. for 3 days to release 2', 3'-cNMPs from protein L*fliZ*, and then the solution was centrifuged at 12,000 rpm for 20 min. The supernatant was collected.

(2) The supernatant from step (1) was ultrafiltrated by means of an ultrafiltration tube having a molecular weight cut-off of 3,000 Da to remove proteins. The filtrate was collected, which was a solution containing four kinds of 2', 3'-cNMPs.

2. Purification of Four Kinds of 2', 3'-cNMPs (2', 3'-cAMP, 2', 3'-cGMP, 2', 3'-cCMP and d2', 3'-cUMP).

(1) The four kinds of 2', 3'-cNMPs in the solution obtained from step 1 were separated by high-performance liquid chromatographic (HPLC) on a $C_{18}$ reversed-phase column, and each kind of 2', 3'-cNMPs was separately collected.

The mobile phases used in the gradient program were as follows: buffer A (10 mM ammonium acetate, pH 5.0) and buffer B (75% (v/v) buffer A, 25% (v/v) methanol).

(2) The protocol used for purification was as follows (the values are times in minutes and percentage of buffer B used): 0.0, 0; 2.5, 0; 5.0, 30; 10.0, 60; 14.0, 100; 21.0, 100; 22.0, 50 and 23.0, 0 at a flow rate of 10 ml/min. The detection wavelength was 254 nm.

HPLC separation of four kinds of 2', 3'-cNMPs was shown in FIG. 3. HPLC and LC-MS analyses of each kind of 2', 3'-cNMPs were shown in FIGS. 4-7.

3. Determination of the Yield of 2', 3'-cNMPs.

(1) Standard 2', 3'-cNMP of each kind was diluted with distilled water to a concentration gradient as follows: 0, 20, 40, 60, 80 and 100 μM. The standard solutions were analyzed by HPLC using a $C_{18}$ reversed-phase column.

The regression equations of the standard curves were generated based on the concentrations of the standards and the corresponding peak areas.

(2) The concentrations of four kinds of 2', 3'-cNMP were calculated based on their respective regression equations. Based on the results, the yields of four kinds of 2', 3'-cNMP from 1 L fermentation broth was determined to be 1.30±0.17 μmol 2', 3'-cCMP, 1.40±0.12 μmol 2', 3'-cUMP, 2.81±0.25 μmol 2', 3'-cGMP and 2.61±0.19 μmol 2', 3'-cAMP. Therefore, about 2.5 mg 2', 3'-cNMPs could be extracted from 1 L fermentation broth in the present invention.

What is claimed is:

1. A recombinant vector, containing a gene L*fliZ* having nucleotide sequence as shown in SEQ ID NO:1.

2. The recombinant vector according to claim 1, wherein the recombinant vector is constructed with a plasmid pET-22b (+).

3. The recombinant vector according to claim 1, wherein the recombination vector is transformed into a host cell yields a recombinant cell.

4. The recombinant vector according to claim 3, wherein the host cell is *E. coli*.

5. The recombinant vector according to claim 4, wherein the *E. coli* is *E. coli* BL21 (DE3).

6. A process for preparing 2',3'-cyclic nucleoside monophosphates (2',3'-cNMPs) by using a gene L*fliZ*, wherein the gene L*fliZ* having nucleotide sequence as shown in SEQ ID NO:1; cloning the gene L*fliZ* into a plasmid as a recombinant vector that is transformed into a host cell that yields as a recombinant cell; culturing the recombinant cell in a fermentation medium; then, preparing the 2', 3'-cNMPs from the recombinant cell.

7. The process according to claim 6, wherein the plasmid is pET-22b (+); the host cell is *E. coli*.

8. The process according to claim 6, wherein the fermentation medium is LB medium.

9. A process for preparing 2', 3'-cNMPs by using a gene L*fliZ*, wherein the gene L*fliZ* having nucleotide sequence as shown in SEQ ID NO:1; cloning the gene L*fliZ* into a plasmid as a recombinant vector that is transformed into a host cell that yields as a recombinant cell; culturing the recombinant cell in a fermentation medium; breaking the recombinant cells and purifying a recombinant protein L*fliZ* having the amino acid sequence shown as SEQ ID NO:2; incubating the recombinant protein L*fliZ* in a recombinant protein L*fliZ* solution; and preparing the 2', 3'-cNMPs from the recombinant protein L*fliZ* solution.

10. The process according to claim 9, wherein the plasmid is pET-22b (+); the host cell is *E. coli*.

11. The process according to claim 9, wherein the fermentation medium is LB medium.

12. The process according to claim 9, wherein the recombinant protein L*fliZ* solution is consisting of 10 mM Tris-HCl, 100 mM NaCl, pH 7.5.

* * * * *

SEQUENCE LISTING

```
<160> NUMBER OF SEQ ID NOS: 4

<210> SEQ ID NO 1
<211> LENGTH: 402
<212> TYPE: DNA
<213> ORGANISM: Pseudoalteromonas sp. S9

<400> SEQUENCE: 1
atgagtaacc aatcagaaac taaacgaagt tacaaaagat ggaatttaaa cctcaaagat      60
```

```
aattacgagc cagagtcagt tcagcttggc ggggtgggcg tacagttact tcgccgctgc    120
tttattgata ttccactttg tcatggcgtt gcaaaagaca ttagcgtggg tggtgtgggt    180
ttattagtgc ctgctgaaaa ggctattcct gacaaattta ttgtggtttt tgataaagcc    240
aatcgattga ctggcaaggt aacgtaccgc cgcgaagtaa gtgacaagtt agtgttttta    300
ggggttgagt ggataagtaa aaatgagcgc ctacgcagcg atatagttaa ccatttacag    360
ttacaagccc aattaaaaaa agcaaaaaaa accaatgcat ag                       402
```

<210> SEQ ID NO 2
<211> LENGTH: 133
<212> TYPE: PRT
<213> ORGANISM: Pseudoalteromonas sp. S9

<400> SEQUENCE: 2

```
Met Ser Asn Gln Ser Glu Thr Lys Arg Ser Tyr Lys Arg Trp Asn Leu
1               5                   10                  15

Asn Leu Lys Asp Asn Tyr Glu Pro Glu Ser Val Gln Leu Gly Gly Val
            20                  25                  30

Gly Val Gln Leu Leu Arg Arg Cys Phe Ile Asp Ile Pro Leu Cys His
        35                  40                  45

Gly Val Ala Lys Asp Ile Ser Val Gly Gly Val Gly Leu Leu Val Pro
    50                  55                  60

Ala Glu Lys Ala Ile Pro Asp Lys Phe Ile Val Val Phe Asp Lys Ala
65                  70                  75                  80

Asn Arg Leu Thr Gly Lys Val Thr Tyr Arg Arg Glu Val Ser Asp Lys
                85                  90                  95

Leu Val Phe Leu Gly Val Glu Trp Ile Ser Lys Asn Glu Arg Leu Arg
            100                 105                 110

Ser Asp Ile Val Asn His Leu Gln Leu Gln Ala Gln Leu Lys Lys Ala
        115                 120                 125

Lys Lys Thr Asn Ala
    130
```

<210> SEQ ID NO 3
<211> LENGTH: 26
<212> TYPE: DNA
<213> ORGANISM: Artificial Sequence
<220> FEATURE:
<223> OTHER INFORMATION: It is synthesized.

<400> SEQUENCE: 3

```
ggaattccat atgagtaacc aatcag                                          26
```

<210> SEQ ID NO 4
<211> LENGTH: 27
<212> TYPE: DNA
<213> ORGANISM: Artificial Sequence
<220> FEATURE:
<223> OTHER INFORMATION: It is synthesized.

<400> SEQUENCE: 4

```
ccgctcgagt gcattggttt tttttgc                                         27
```